US009903860B2

(12) United States Patent
Arnold et al.

(10) Patent No.: US 9,903,860 B2
(45) Date of Patent: Feb. 27, 2018

(54) CHARACTERIZING LIQUIDS USING MAGNETIC DISCS

(71) Applicant: University of Florida Research Foundation, Inc., Gainesville, FL (US)

(72) Inventors: David P. Arnold, Gainesville, FL (US); Nicolas Garraud, Gainesville, FL (US)

(73) Assignee: UNIVERSITY OF FLORIDA RESEARCH FOUNDATION, INCORPORATED, Atlanta, GA (US)

( * ) Notice: Subject to any disclaimer, the term of this patent is extended or adjusted under 35 U.S.C. 154(b) by 0 days.

(21) Appl. No.: 15/314,297

(22) PCT Filed: May 28, 2015

(86) PCT No.: PCT/US2015/032967
§ 371 (c)(1),
(2) Date: Nov. 28, 2016

(87) PCT Pub. No.: WO2015/184133
PCT Pub. Date: Dec. 3, 2015

(65) Prior Publication Data
US 2017/0097338 A1   Apr. 6, 2017

Related U.S. Application Data

(60) Provisional application No. 62/004,404, filed on May 29, 2014.

(51) Int. Cl.
  *G01N 33/553* (2006.01)
  *G01N 33/543* (2006.01)
  *G01N 27/74* (2006.01)
  *G01N 21/17* (2006.01)

(52) U.S. Cl.
  CPC ..... *G01N 33/5434* (2013.01); *G01N 21/1717* (2013.01); *G01N 27/74* (2013.01); *G01N 2021/1727* (2013.01)

(58) Field of Classification Search
None
See application file for complete search history.

(56) References Cited

U.S. PATENT DOCUMENTS

| 4,539,521 A | 9/1985 | Matsumoto |
| 2008/0220411 A1 | 9/2008 | McNaughton et al. |

OTHER PUBLICATIONS

International Search Report for PCT/US2015/023967 dated Aug. 26, 2015.
Garraud, N "Characterization of fluids via measurement of the rotational dynamics of 1-32 suspended magnetic microdiscs". Journal of Applied Physics, vol. 117, No. 17, Apr. 22, 2014, 17B320 [online], [retrieved on Aug. 10, 2015]. Retrieved from the Internet <URL: http:I/scitation.aip.org/content/aip/journal/jap/117/17/10.1063/1.4918784> <DOI: 10.1063/1.4918784>.

*Primary Examiner* — Chris L Chin
(74) *Attorney, Agent, or Firm* — Thomas | Horstemeyer, LLP

(57) ABSTRACT

The present disclosure is directed towards characterizing liquids through the use of magnetic discs that rotate in response to dynamic magnetic fields. In some embodiments, a light beam is transmitted into the liquid while the magnetic discs rotate, and one or more parameters a light beam signal associated with the transmitted light beam are identified. Various characteristics of the liquid may be detected based on the one or more parameters of the light beam signal.

34 Claims, 14 Drawing Sheets

CHARACTERIZING LIQUIDS USING MAGNETIC DISCS

CROSS-REFERENCE TO RELATED APPLICATION

This application is the 35 U.S.C. § 371 national stage application of PCT Application No. PCT/US2015/032967, filed May 28, 2015, where the PCT claims priority to copending U.S. provisional application entitled, "Characterizing Liquids Using Magnetic Discs," having serial number 62/004,404, filed May 29, 2014, both of which are entirely incorporated herein by reference.

TECHNICAL FIELD

The present disclosure is generally related to the detection of fluid characteristics.

BACKGROUND

There is great interest to study fluidic properties and/or biological activity within fluids in a remote and non-invasive manner. For example, the suspension of magnetic discs is of interest in tagging, trapping, actuating, or interrogating biological samples.

SUMMARY

Embodiments of the present disclosure provide a system and method for detecting fluid characteristics in the presence of a magnetic field.

An embodiment of the present disclosure provides for a system comprising a magnetic field generator configured to expose a liquid to a dynamic magnetic field, wherein a plurality of magnetic discs are suspended in the liquid, wherein the dynamic magnetic field causes the plurality of magnetic discs to rotate in the liquid. The system further includes a light source configured to transmit a light beam into the liquid, wherein the light beam transmitted into the liquid is responsive to the plurality of magnetic discs being rotated in the liquid; a light sensor configured to detect a portion of the light beam from the liquid; and at least one computing device. The at least one computing device is configured obtain a light beam signal that corresponds to a detected portion of the light beam, detect a parameter of the light beam signal, and detect a characteristic of the liquid based on the parameter of the light beam signal.

An embodiment of the present disclosure further provides for a method comprising exposing a liquid to a dynamic magnetic field, wherein a plurality of magnetic discs are suspended in the liquid, wherein the dynamic magnetic field causes the plurality of magnetic discs to rotate in the liquid; transmitting a light beam into the liquid, wherein the light beam transmitted into the liquid is responsive to the plurality of magnetic discs being rotated in the liquid; obtaining, using at least one computing device, a light beam signal that corresponds to a detected portion of the light beam; detecting, using the at least one computing device, a parameter of the light beam signal; and detecting, using the at least one computing device, a characteristic of the liquid based on the parameter of the light beam signal.

An embodiment of the present disclosure additionally provides for a method comprising exposing a liquid to a dynamic magnetic field, wherein a plurality of magnetic discs are suspended in the liquid, wherein the dynamic magnetic field causes the plurality of magnetic discs to rotate in the liquid, wherein at least a subset of the plurality of magnetic discs comprise a targeting material having an affinity for an agent; transmitting a light beam into the liquid, wherein the light beam transmitted into the liquid is responsive to the plurality of magnetic discs being rotated in the liquid; obtaining, using at least one computing device, a light beam signal that corresponds to a detected portion of the light beam; detecting, using the at least one computing device, a parameter of the light beam signal; and detecting, using the at least one computing device, whether the agent is present in the liquid based on the parameter of the light beam signal.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

The present disclosure is directed towards characterizing liquids through the use of magnetic discs that rotate in response to dynamic magnetic fields. In some embodiments, a light beam is transmitted through the liquid while the magnetic discs rotate, and one or more parameters of the transmitted light beam are identified. Various characteristics of the liquid may be detected based on the one or more parameters of the light beam that has been transmitted through the liquid.

Figure 1A:
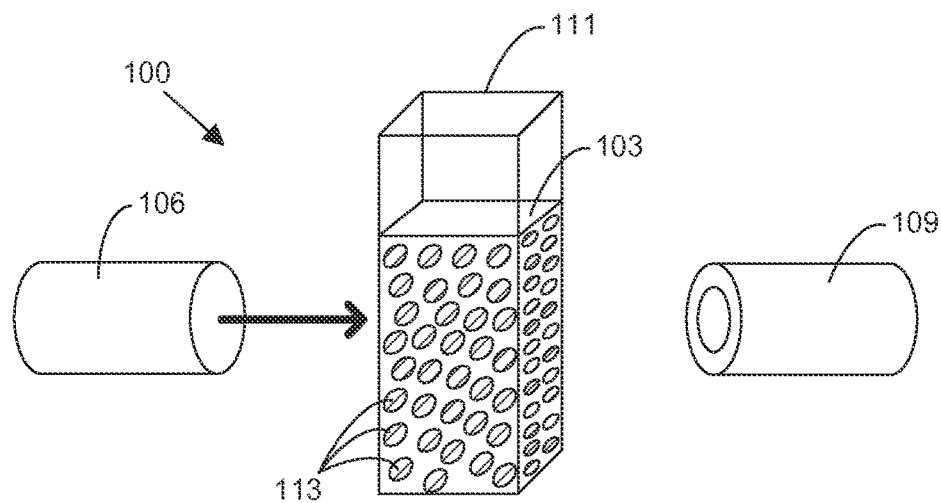
FIGS. 1A-1B are diagrams of a liquid characterization system used to detect various characteristics of a liquid according to various embodiments of the present disclosure.

With reference to FIG. 1A, shown is an example of a liquid characterization system 100 used to detect various characteristics of a liquid 103 according to various embodiments. The liquid characterization system 100 may include a light source 106, a light sensor 109, a magnetic field generator (not shown), one or more computing devices (not shown), and/or other components.

The liquid 103 may be contained within a container 111. The liquid 103 and the container 111 may be at least partially transparent to light. In an embodiment, the liquid can include an aqueous solution, a polymer solution, a fluid with particulates, a biological fluid, or the like.

Additionally magnetic discs 113 may be suspended in the liquid 103. Further description regarding the magnetic discs 113 is provided below.

The magnetic field generator creates a dynamic magnetic field, such as a magnetic field that rotates relative to the liquid 103. In some embodiments, the magnitude of the dynamic magnetic field may range from about 0.1 mT to about 10 mT. As will be described in further detail below, the dynamic magnetic field may cause the magnetic discs 113 to change in physical orientation relative to the container in which the liquid 103 is held. The magnetic field generator in some embodiments may comprise two transverse coils. In alternative embodiments, the magnetic field generator may comprise two-axis Helmholtz coils. In alternative embodiments, the magnetic field generator may comprise a Helmholtz coil pair and a transverse coil. By using two orthogonally-oriented coils, the dynamic magnetic field to which the liquid 103 is exposed may be substantially homogeneous in space. In some embodiments, the supply currents for the magnetic field generator may be sinusoidal, resulting in a rotating magnetic field having a magnitude that is substantially constant. In other embodiments, the dynamic magnetic field may be generated by physically rotating one or more permanent magnets.

Additionally, the frequency at which the dynamic magnetic field rotates may be swept across a frequency range. As a non-limiting example, the frequency of the dynamic magnetic field may be swept from about 1 Hz to about 40 Hz or from 10 Hz to 200 Hz. In some embodiments, the supply voltages for the magnetic field generator may be dynamically adjusted in order to cause the magnitude of the dynamic magnetic field to be substantially constant as the frequency of the dynamic magnetic field is changed.

The light source 106 generates a light beam 116. In some embodiments the light beam 116 may have spectral content that is narrowband or wideband according to various embodiments. In some embodiments, the light source 106 may comprise a laser. The light beam 116 generated by the light source 106 may be infrared light, visible light, and/or ultraviolet light according to various embodiments. As shown in FIG. 1A, the light source 106 and the liquid 103 are positioned so that the liquid 103 is exposed to the light beam 116. The magnetic discs 113 suspended in the liquid 103 reflect and/or absorb a portion of the light beam 116, while another portion of the light beam 116 is transmitted through the liquid 103. As will be described in further detail below, the amount of the light beam 116 that is transmitted through (or reflected by) the liquid 103 is dependent upon the physical orientation of the magnetic discs 113 relative to the light beam 116.

Figure 1B:
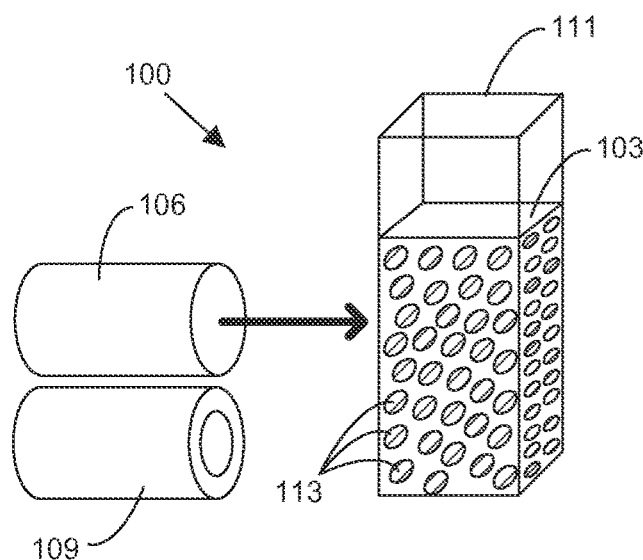

The light sensor 109 is a device that is configured to detect the intensity of the portion of the light beam 116 that has been transmitted through the liquid 103, in one embodiment. Further, in various embodiments, the light sensor 109 may be positioned to detect a portion of the light beam 116 that is reflected from the liquid 103, as shown in FIG. 1B. In some embodiments, the light sensor 109 may be positioned at a specific orientation relative to the light source 106 so as to maximize the variation in the transmitted or reflected light. It is further noted that, while working in a reflection configuration, the light sensor 109 may be aligned with the light source 103 as shown in FIG. 1B, but also perpendicular to it, above the container, or in any other direction in various embodiments. In some embodiments, the light sensor 109 may comprise a photodiode coupled to one or more computing devices. The intensity of the light beam 116 detected by the light sensor 109 may be recorded over time using the one or more computing devices.

Figure 2:
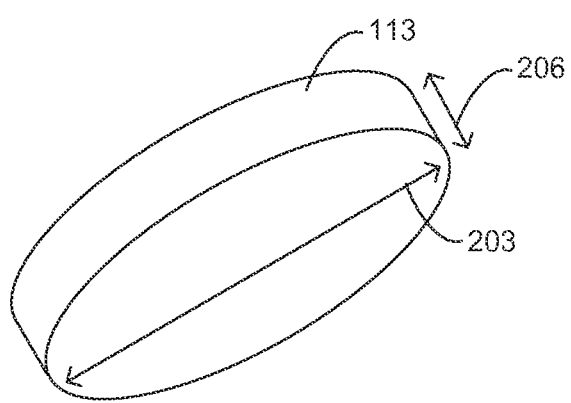
FIG. 2 is a diagram of a magnetic disc according to various embodiments of the present disclosure.

With reference to FIG. 2, shown is an example of one of the magnetic discs 113 according to various embodiments. The magnetic disc 113 may be a soft ferromagnetic disc having a thickness 206 that is less than a diameter 203 of the magnetic disc 113. In an embodiment, the soft ferromagnetic material can be Ni, Fe, Co, Ni-Fe alloy, permalloy, a Ni-Fe-Mo alloy, supermalloy, any other suitable material, or any combination thereof. In various embodiments, the magnetic disc(s) 113 may also be a composite of several layers, such as gold. In particular, a covering of gold on the magnetic disc can provide a protection of magnetic material and biocompatibility, which can also increase the affinity of bio-markers. The magnetic disc 113 may have a diameter 203 of about 0.1 µm to about 5 µm, and a thickness 206 of about 10 nm to about 500 nm. The magnetic disc 113 (e.g., circular or oval-shaped discs) may exhibit a spin vortex of a magnetic ground state, resulting in a closed magnetic spin arrangement. As a result, the magnetic disc 113 may exhibit zero or near-zero magnetic remanence. By virtue of the zero or near-zero magnetic remanence, the magnetic discs 113 may not agglomerate with each other when in suspension in the liquid 103.

Because a magnetic structure tends to rotate to align its easy-axis relative to a magnetic field, the physical orientation of the magnetic discs 113 in the liquid 103 may adjust responsive to the dynamic magnetic field created by the magnetic field generator. For example, if the dynamic magnetic field rotates relative to the container 111, dynamic magnetic field may cause the magnetic discs 113 to rotate in the liquid 103.

The rotation of the magnetic discs 113 may be affected by the characteristics of the liquid 103 in which the magnetic discs 113 are suspended. For example, the viscosity and/or other characteristics of the liquid 103 may affect the phase difference between the rotation of the magnetic discs 113 and the rotation of the dynamic magnetic field and/or other aspects of the rotation. Therefore, a fluid characteristic may be determined based on the disc behavior in presence of the magnetic field.

In some embodiments, at least a subset of the magnetic discs 113 may comprise a targeting material having an affinity for an agent. In an embodiment, the targeting material can be disposed on the disc, for example, as a coating on the disc or on a portion of the disc. In an embodiment, the targeting material may be disposed only on one face of the disc. In another embodiment the targeting material may be disposed only on the circumferential perimeter of the disc. In an embodiment, the targeting material can function to cause the agent in the liquid to interact (e.g., be attracted to, bond, and the like) with the disc. In an embodiment, the targeting material can have an affinity for a cell, a tissue, a protein, DNA, RNA, an antibody, an antigen, a compound, and the like. In particular, the targeting material can function to target specific bacterial cells. In an embodiment, the targeting material can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, aptamers, small molecules, or combinations thereof, that have an affinity for one or more agents. Thus, if an agent is present in the liquid 103, the agent may bind to at least some of the magnetic discs 113.

An agent being bound to a magnetic disc 113 may affect the rotation of the magnetic disc 113 when exposed to the dynamic magnetic field. For example, the bound agent (e.g., bacterial cell) may increase the hydrodynamic diameter and/or the overall mass of the magnetic disc 113 and thereby affect the rotation of the magnetic disc 113. In some embodiments, the agent being bound to the magnetic disc 113 may affect the phase difference between the rotation of the magnetic discs 113 and the rotation of the dynamic magnetic field and/or other aspects of the rotation. Thus, a fluid characteristic of the agent in the fluid may be determined based on the disc behavior in the presence of the magnetic field.

As mentioned above, the magnetic discs 113 suspended in the liquid 103 reflect and/or absorb a portion of the light beam 116, while another portion of the light beam 116 is transmitted through the liquid 103. In particular, the amount of the light that is transmitted through the liquid 103 is dependent upon the orientation of the magnetic discs 113 relative to the light beam 116. For example, the maximum amount of the light beam 116 may be transmitted through the liquid 103 when the disc axis (i.e., the axis perpendicular to the diameter 203) is perpendicular to the light beam 116. By contrast, the minimum amount of the light beam 116 may be transmitted through the liquid 103 when the disc axis is aligned with the light beam 116. Thus, the magnetic discs 113 may function as an optical shutter for the light beam 116. Because the dynamic magnetic field causes the magnetic discs 113 to rotate in the liquid 103, the intensity of the light beam 116 that transmitted through the liquid 103 may be modulated by the magnetic discs 113.

Figure 3A:
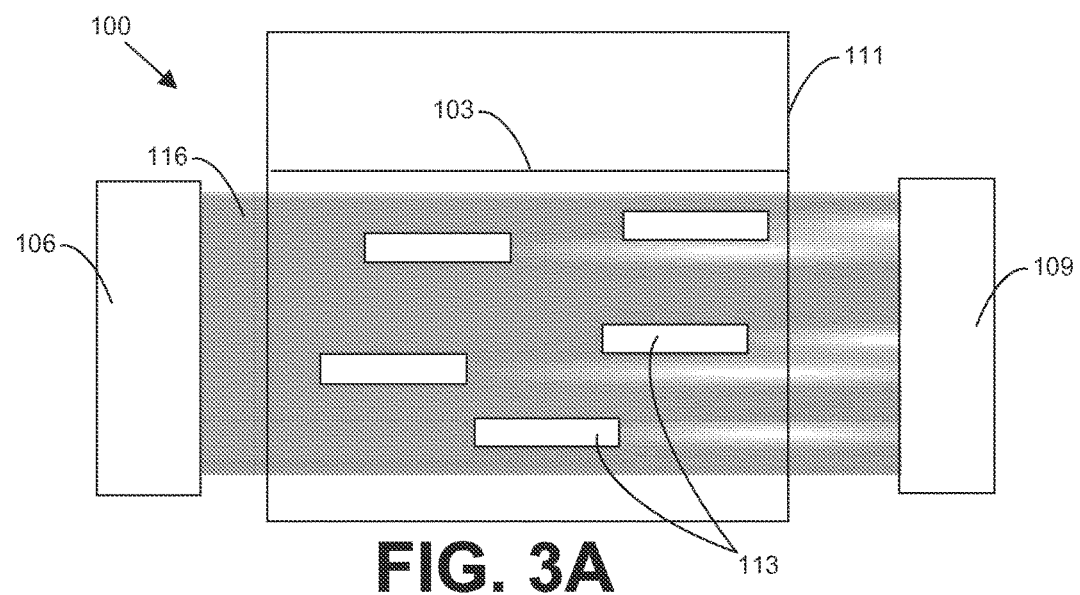
FIGS. 3A-3B are diagrams illustrating a transmission of a light beam through a liquid as a function of the orientation of magnetic discs according to various embodiments of the present disclosure.
Figure 3B:
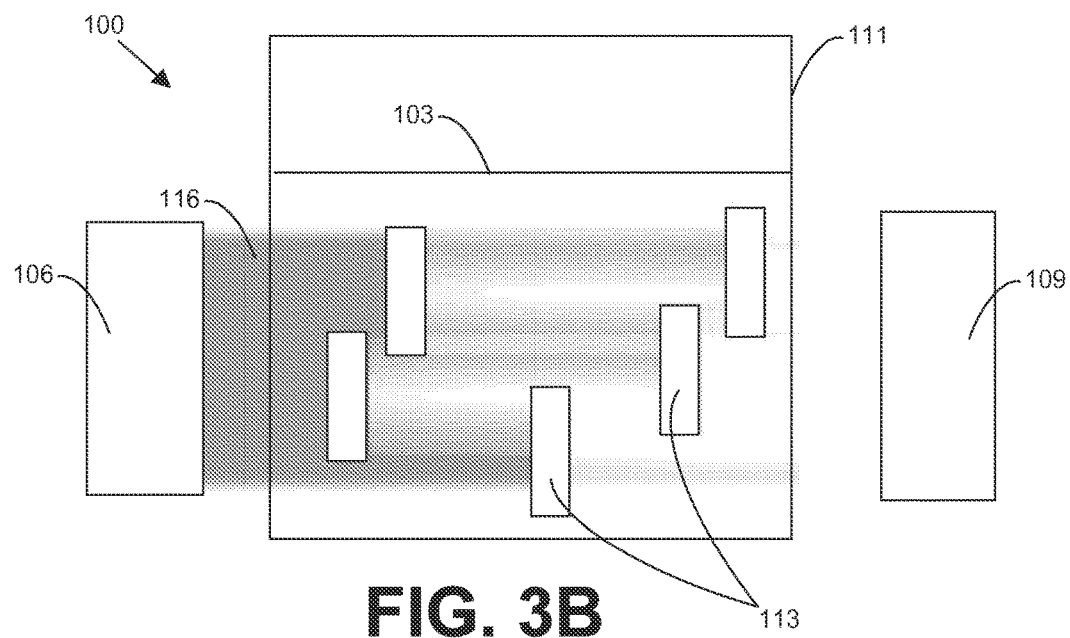

FIGS. 3A-3B illustrate the transmission of the light beam 116 through the liquid 103 as a function of the orientation of the magnetic discs 113. In FIG. 3A, the dynamic magnetic field has caused the magnetic discs 113 to be oriented such that the longitudinal axes of the magnetic discs 113 are perpendicular to the light beam 116. In this orientation, the amount of the light beam 116 that is reflected and/or absorbed by the magnetic discs 113 is at its minimum. Accordingly, the intensity of the light beam 116 that is detected by the light sensor 109 is at its maximum.

By contrast, in FIG. 3B, the dynamic magnetic field has caused the magnetic discs 113 to be oriented such that the longitudinal axes of the magnetic discs 113 are aligned with the light beam 116. In this orientation, the amount of the light beam 116 that is reflected and/or absorbed by the magnetic discs 113 is at its maximum. Accordingly, the intensity of the light beam 116 that is detected by the light sensor 109 is at its minimum.

Figure 4:
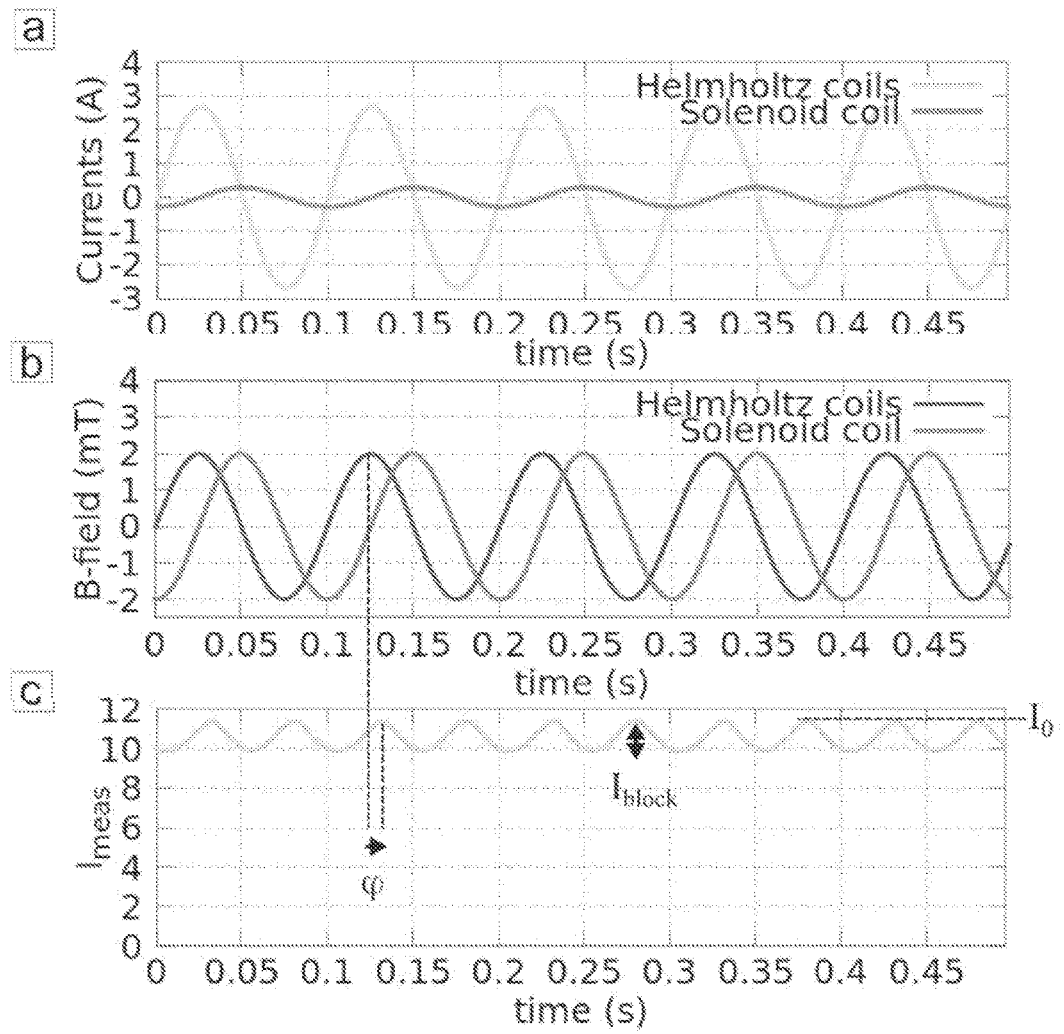
FIG. 4 is a diagram of plots A-C that illustrate an intensity of a light beam that is transmitted through a liquid relative to a dynamic magnetic field and the electrical currents supplied to a magnetic field generator according to various embodiments of the present disclosure.

With reference to FIG. 4, shown are plots A-C that illustrate the intensity of the light beam 116 that is transmitted through the liquid 103 relative to the dynamic magnetic field and the electrical currents supplied to the magnetic field generator according to various embodiments. In particular, plot A shows time series of the magnitudes of the electrical currents supplied to the magnetic field generator, plot B shows time series of magnitudes of the dynamic magnetic fields generated by the magnetic field generator, and plot C shows a time series of the intensity of the light beam 116 transmitted through the liquid 103. In the example shown in FIG. 4, the magnitude and the frequency of the dynamic magnetic field is relatively constant over time. However, in alternative embodiments, the magnitude, the frequency, and/or other parameters of the dynamic magnetic field may be varied over time. For example, in one embodiment, the frequency of the dynamic magnetic field may be swept across a predetermined frequency range while the magnitude of the dynamic magnetic field is held substantially constant. In another embodiment, the frequency of the dynamic magnetic field may be held substantially constant while the magnitude of the dynamic magnetic field is swept across a predetermined field magnitude range.

In the example shown in FIG. 4, $\phi$ represents the phase shift between the dynamic magnetic field and the intensity of the light beam 116 that has been transmitted through the liquid 103. $I_{block}$ represents the maximum amount of light intensity that has been blocked by the magnetic discs 113, and $I_o$ represents the maximum intensity of the light beam 116 that has been transmitted through the liquid 103. The phase shift $\phi$, the maximum amount of blocked light $I_{block}$, the maximum amount of transmitted light $I_o$, and/or other parameters of the light beam 116 may be used to determine various characteristics of the liquid 103. For example, a computing device may compare the values for one or more parameters of the light beam 116 to values obtained using samples with known characteristics. If the values for the light beam 116 match one or more values obtained from a sample with known characteristics, the computing device may determine that one or more characteristics of the liquid 103 is the same or is similar to the corresponding sample. Thus, embodiments of the present disclosure may be used to detect various characteristics of a liquid 103, such as the viscosity of the liquid 103, whether an agent is present in the liquid 103, and/or other characteristics.

Figure 5:
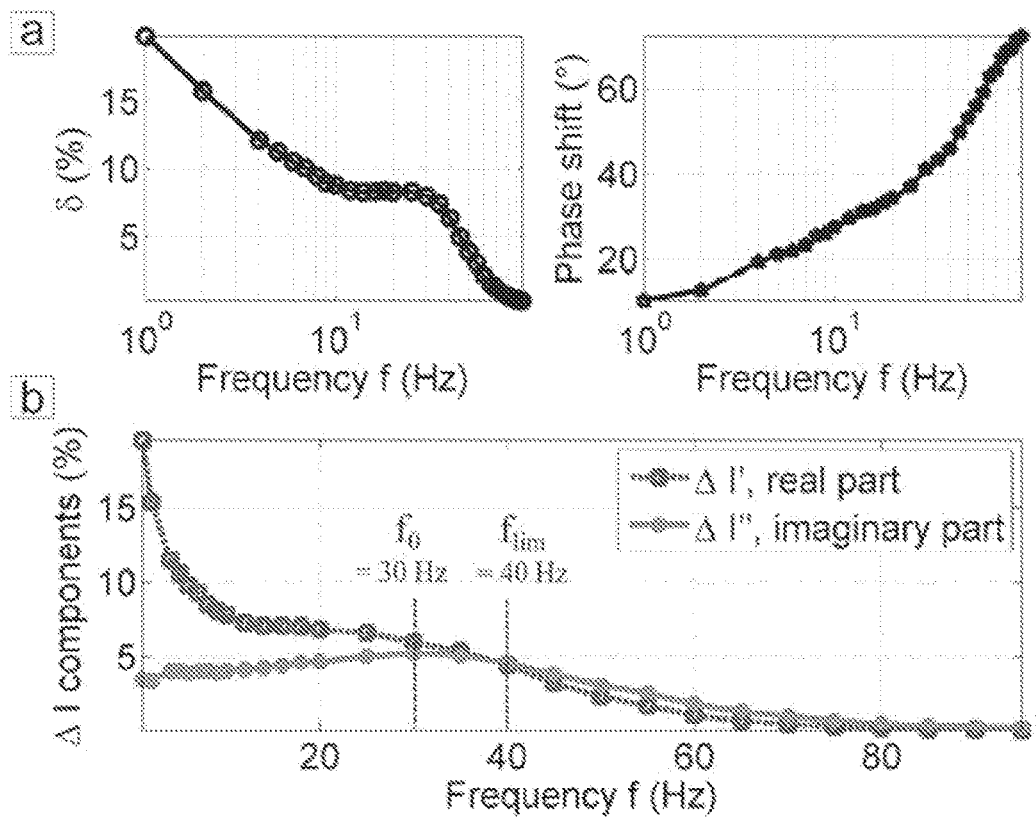
FIG. 5 is a diagram of plots A-B that illustrate that a light beam that has been transmitted through a liquid may depend on a frequency of a dynamic magnetic field according to various embodiments of the present disclosure.

With reference to FIG. 5, shown are plots A-B that illustrate that the light beam 116 that has been transmitted through the liquid 103 may depend on the frequency of the dynamic magnetic field. In particular, plot A illustrates the relationships between (i) the amplitude of the intensity of the light beam 116 as the frequency of the dynamic magnetic field is adjusted while the magnitude is held constant and (ii) the phase difference between the light beam 116 and the dynamic magnetic field as the frequency of the dynamic magnetic field is adjusted and the magnitude is held constant. As shown, the intensity of the light beam 116 may generally decrease as the frequency of the dynamic magnetic field increases. Additionally, the phase difference may generally increase as frequency of the dynamic magnetic field increases.

Plot B illustrates the real and imaginary components of the light beam 116 as the frequency of the dynamic magnetic field is adjusted. The peak of the imaginary component of the light beam 116 may be a parameter that is used to characterize the liquid 103.

Figure 6:
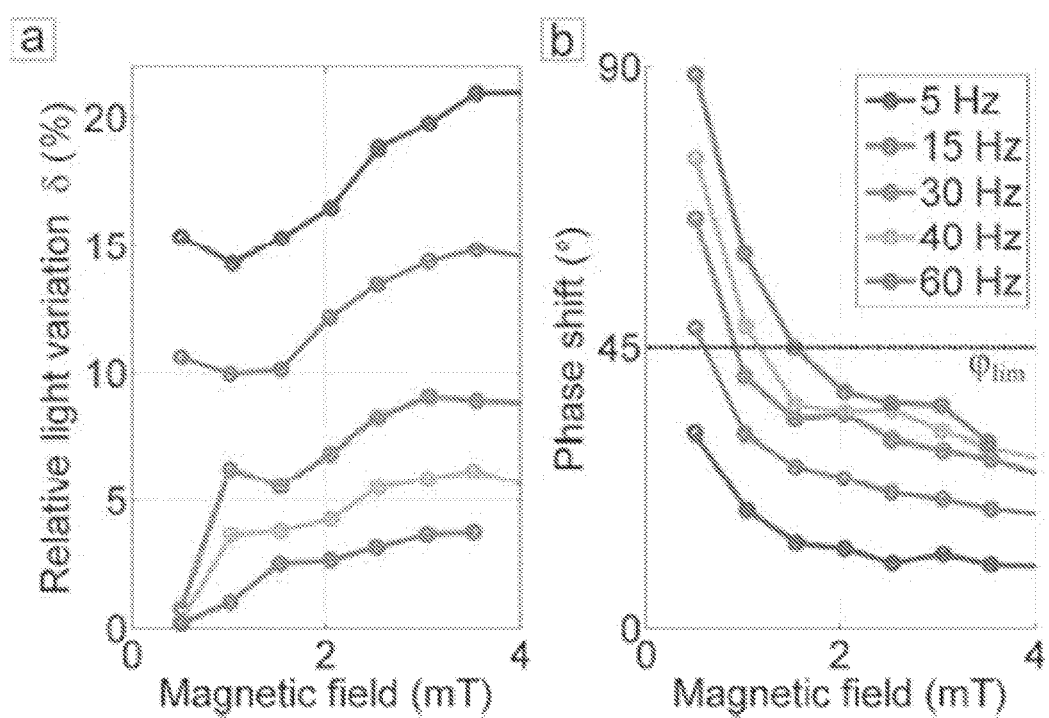
FIG. 6 is a diagram of plots A-B that illustrate that a light beam that has been transmitted through a liquid may be dependent on a magnitude of a dynamic magnetic field according to various embodiments of the present disclosure.

With reference to FIG. 6, shown are plots A-B that illustrate that the light beam 116 that has been transmitted through the liquid 103 may be dependent on the magnitude of the dynamic magnetic field. In particular, plot A shows the relative variation of the intensity of the light beam 116 as the magnitude of the dynamic magnetic field is adjusted and the frequency is held constant. Plot B shows the phase difference between the light beam 116 and the dynamic magnetic field as the magnitude of the dynamic magnetic field is adjusted and the frequency is held constant. As shown in plot B, the phase difference may generally decrease as the magnitude of the dynamic magnetic field increases.

Figure 7:
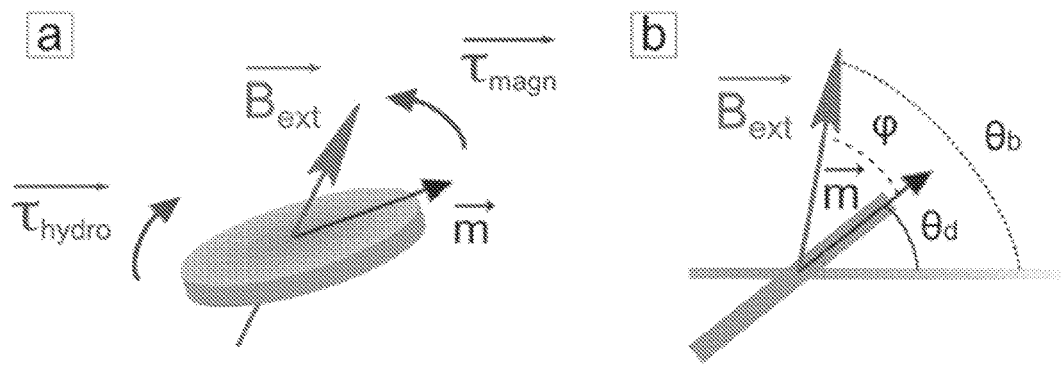
FIG. 7 is a diagram of plots A-B that illustrate the torque forces subjected to a magnet disc and the resulting phase shift derived from the torque forces in accordance with embodiments of the present disclosure.

Additional illustrative examples are provided in the following figures and accompanying discussion. With reference to FIG. 7, shown are plots A-B that illustrate the torque forces subjected to a magnet disc in accordance with embodiments of the present disclosure and the resulting phase shift derived from the torque forces.

As shown, at steady state, and for a given magnetic field magnitude, the phase shift $\phi$ can be derived from the balance between the magnetic torque $\tau_{magn}$ and the hydrodynamic torque $\tau_{hydro}$ (Plot A of FIG. 7), each of which depends on the disc and fluid parameters, like the disc dimensions and the fluid viscosity. Hence, monitoring of the phase shift $\phi$ can provide a valuable method for interrogation of one or more of these properties.

The external magnetic field $\vec{B}_{ext}$ modulated at $\omega=2\pi f$ makes an angle $\theta_b=\omega t$ with the light path, whereas a disc 113 makes an angle $\theta_d$ with respect to the light path (Plot B of FIG. 7). The angle difference between the disc plane and the magnetic field is the phase shift $\phi$. Due to their small size dispersion, all the discs 113 are assumed to have the same magnetic and mechanical behavior. Therefore, the recorded light intensity $I_{meas}$ depends on $\theta_d=\omega t-\phi$.

$$I_{meas}=I_0(1-\Delta I)=I_0(1-|\sin\theta_d|) \quad \text{(Equation 1)}$$

$I_0$ is the measured light without any discs in the solution, which depends on the optical system. $\Delta I$ is the percentage of light blocked by the discs 113 in suspension and depends on the projection of the disc area in a plane perpendicular to the light path, the disc concentration in the solution, and the length of the light path. For one mechanical revolution of the discs 113, there are two variations in intensity (mathematically represented by the rectified sine term), and hence the light is modulated at a double frequency 2f. The disc behavior can also be described by the in-phase $\Delta I'$ and the out-of-phase $\Delta I''$ components of the signal variation $\Delta$, defined by $$\Delta I'=\delta\cos\phi, \quad \Delta I''=\delta\sin\phi \quad \text{(Equation 2)}$$

By neglecting the angular moment of inertia (which is assumed to be small), the equation of motion of a magnetic disc 113 in a uniform magnetic field is given by the equilibrium of the magnetic and the hydrodynamic torques $$\vec{\tau}_{magn}+\vec{\tau}_{hydro}=\vec{0} \quad \text{(Equation 3)}$$

The magnetic field is chosen low enough to operate in the linear range of the disc magnetization curve, described by the initial susceptibility $\chi_0$. Moreover, due to its high shape anisotropy, the magnetic moment $\vec{m}$ of a flat vortex disc remains mainly in-plane, even when $\vec{B}_{ext}$ presents an out-of-plane component. Hence, the magnetic moment is given by $$|\vec{m}|=Vol_{\chi_0}|\vec{H}_{ext}|_{in-plane}=\frac{Vol_{\chi_0}}{\mu_0}|\vec{B}_{ext}|\cos\varphi. \quad \text{(Equation 4)}$$

The magnetic torque is thus calculated as $$|\vec{\tau}_{magn}|=|\vec{m}\times\vec{B}_{ext}|=\frac{Vol_{\chi_0}}{2\mu_0}|\vec{B}_{ext}|^2\sin(2\varphi). \quad \text{(Equation 5)}$$

Due to its dependency on $2\phi$, the torque is null when the B-field is in-plane and out-of-plane with respect to the disc ($\phi=0$ or $\phi=\pi/2$), and reaches a maximum for $\phi=\pi/4$. The hydrodynamic torque is given by $$|\tau_{hydro}|=-\eta K_r\dot{\theta}_d=-\eta K_r(\omega-\dot\phi), \quad \text{(Equation 6)}$$

with $\eta$ the fluid viscosity and $K_r$ the rotational resistance depending on the disc dimensions and aspect ratio.

By solving Equation 3, the rotational dynamics of the discs 113 in suspension are governed by a critical frequency limit:

$$\omega_{lim}=|\vec{B}_{ext}|^2\frac{\pi\phi^2 t\chi_0}{8\mu_0\eta K_r}. \quad \text{(Equation 7)}$$

This limit defines two distinct frequency ranges, as found in the dynamics of rotating hard magnetic spheres. In the present case:

(1) $\omega<\{\text{fourth root}\}_{lim}$: The discs 113 rotate synchronously with $\vec{B}_{ext}$. A stable steady-state solution is found for $0<\phi<\pi/4$ $$\varphi=\frac{1}{2}\arcsin\left(\frac{\omega}{\omega_{lim}}\right). \quad \text{(Equation 8)}$$

(2) $\omega>\omega_{lim}$: The discs 113 rotate asynchronously with $\vec{B}_{ext}$ and $\pi/4<\phi<\pi/2$.

It is noted from Equation 8 that the steady-state phase shift depends mainly on the magnetic field parameters ($\omega$ and $\vec{B}_{ext}$) and the magnetic suspension characteristics (the fluid viscosity, the disc sizes, and magnetic properties). It is also noted from Equation 7 that the magnitude of the magnetic field can be adjusted to change $\omega_{lim}$.

Next, experimental testing is presented that focuses on the influence of the magnetic field frequency and magnitude, the fluid viscosity, and the disc concentration on the phase shift and the light amplitude change. For this testing, discs 113 are microfabricated on a silicon substrate using a metal lift-off procedure. Three layers are spin coated: A 200-nm thick PMMA sacrificial layer (A4 MicroChem), a 300-nm thick LOR 3A lift-off layer (MicroChem), and an 800-nm thick S1813 photosensitive layer (Shipley, Microposit). The resist layers are patterned with a dense array of dots by direct-write UV laser at 405 nm (DWL 66fs Heidelberg) and developed to obtain the photoresist mask. A 70-nm-thick permalloy ($Ni_{80}Fe_{20}$) layer is then deposited through the mask by magnetron sputtering followed by metal lift-off in AZ400K (AZ Electronic Materials). A dense array of 2.5 μm diameter, 70 nm thick magnetic discs 113 is obtained on the sacrificial layer. As expected, the characteristic magnetic behavior of the disc array, obtained with a vibrating sample magnetometer (MicroSense EV9), exhibits no remanence. By dissolving the sacrificial PMMA layer in acetone and by rinsing it in deionized water, 30×10⁶ discs are released into 1 ml of water.

The experimental stage combines magnetic actuation with optical detection via a laser light source 106 and photodiode light sensor 109. A rotating magnetic field is created by two perpendicular pairs of Helmholtz coils. The coils are supplied by two sinusoidal current waveforms in quadrature (frequency f) generated by a power amplifier. The amplitude of each waveform is adjusted via a computer-controlled data acquisition system so as to supply equal field intensity on the sample. The volume of the disc suspension interacting with the light beam 116 (2×5×10 mm³) is contained in a glass vial that is placed in the center of the coils so the discs 113 are subjected to a spatially uniform rotating magnetic field up to 2 mT. Together the discs 113, rotating coherently, act as an optical shutter modulating the transmission path of a 650 nm, 5 mW laser. The transmitted light is measured by the photodiode light sensor 109 (Thorlabs DET110) during 0.5 second, and the output signal is analyzed in real time to extract the DC component $I_0$, the relative AC amplitude $\Delta I$, and the phase shift $\phi$ with respect to the current in one coil.

Figure 8:
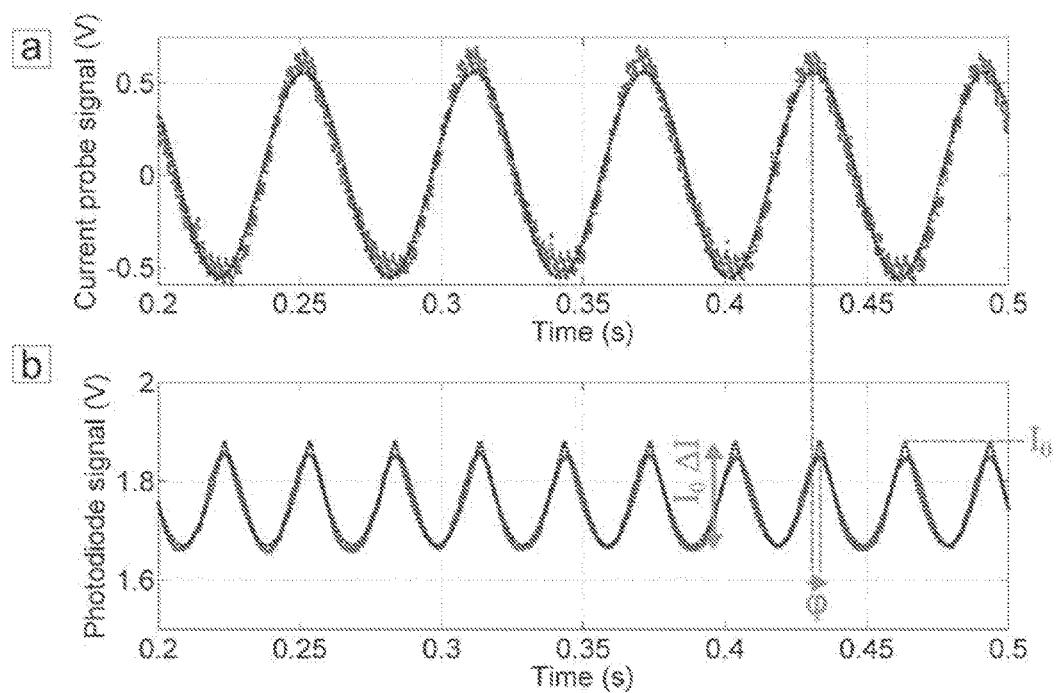
FIG. 8 is a diagram of plots A-B that illustrate recorded signals of a coil current and light intensity modulation according to embodiments of the present disclosure.

With reference to FIG. 8, shown are plots A-B that illustrate recorded signals of one coil current and light intensity modulation according to embodiments of the present disclosure. In particular, Plot B shows an example time-waveform of the light intensity modulation for f=16.5 Hz in water under a 1.5 mT magnitude field. The measured light is, as expected, a rectified sine modulated at 2f=33 Hz and phase-shifted by $\phi$ (Plot B of FIG. 8). Before dynamic experiments, the disc solution is sonicated for 5 minutes to disperse the discs 113 into suspension. Without any surfactant, the discs 113 remain well suspended for at least 1 hour, allowing plenty of time for dynamic experiments.

Figure 9:
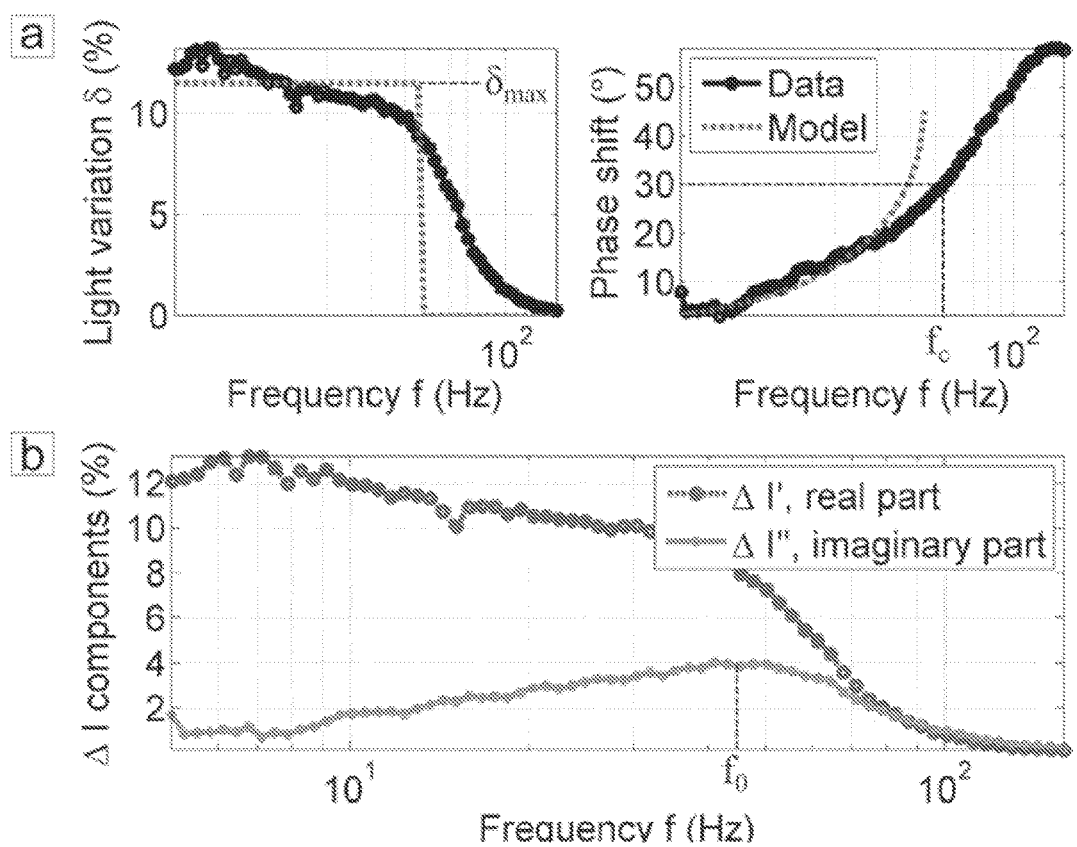
FIG. 9 is a diagram of plots A-B that illustrate the frequency dependence of discs in suspension in water according to embodiments of the present disclosure.

With reference to FIG. 9, shown are plots A-B that illustrate the frequency dependence of discs 113 in suspension in water 103 according to embodiments of the present disclosure. In particular, FIG. 9 shows the typical overall frequency response of the discs 113 in suspension in water 103 subjected to a 1.5 mT rotating magnetic field. The amplitude and phase of $\Delta I$ with model fits are presented in Plot A of FIG. 9. The model described in Equation 8 explains the two observed frequency ranges as the synchronous mode (below 47 Hz) and the asynchronous mode, separated by a transition zone. Below 47 Hz, the disc rotation is synchronous with the external magnetic field and the intensity modulation amplitude $\delta$ is slightly constant and equal to $\delta_{max}$. During the transition zone, the viscous effects from the hydrodynamic torque lead to a large decrease in amplitude, leading to the asynchronous mode. The model described in Equation 8 fits well with the measured phase shift evolution until 30 Hz. The misfit observed above 30 Hz is attributed to complexity in the test experiments (dispersion in the disc properties, complex flow around the discs) that is not accounted for in the basic model. The real $\Delta I'$ and imaginary $\Delta I''$ components are reported in Plot B of FIG. 9. During the synchronous phase, the in-phase signal decreases while the out-of-phase signal increases. During the transition, both signals are attenuated because discs stop their synchronous rotation. This results in a key feature—a maximum in the imaginary part at $f_0$=45 Hz. In ac susceptometry, this peak position is usually extracted in order to follow any change in the disc suspension, such as the fluid viscosity. However, during the present testing, a characteristic frequency $f_c$ is defined for which the phase shift $\phi$ is equal to 30 degrees. This frequency, characteristic of the rotational dynamics, presents a high sensitivity to the suspension changes and has the advantage over $f_0$ to be independent of unexpected changes in $\delta$. The standard deviation of this characteristic frequency is evaluated at 1.5 Hz.

Figure 10:
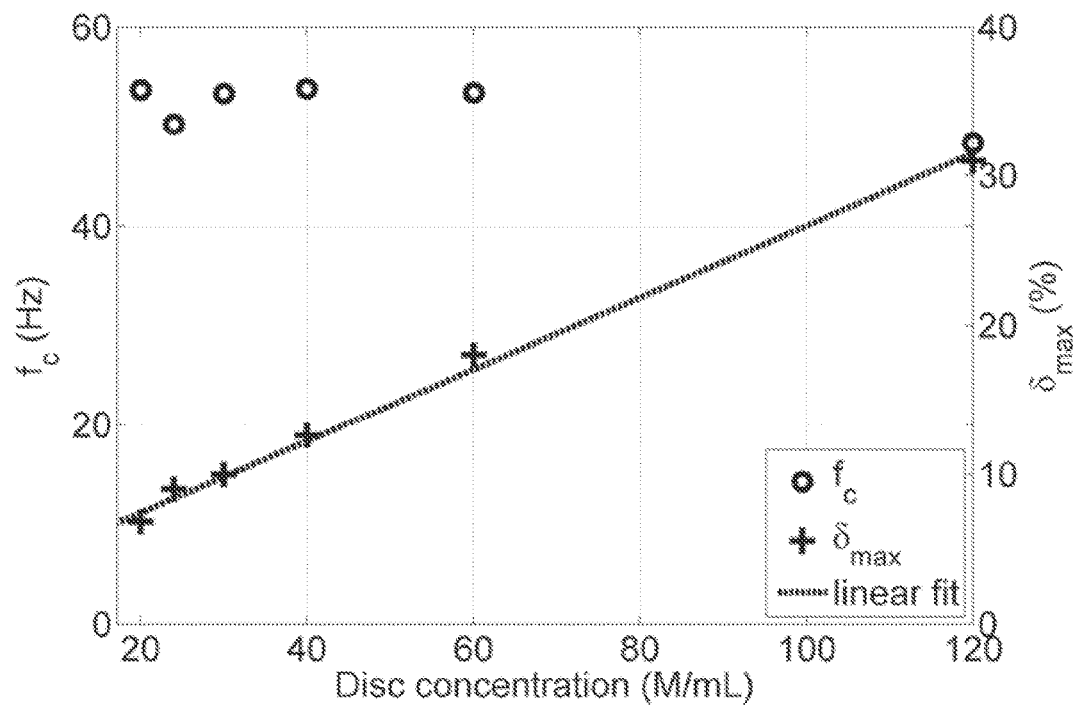
FIG. 10 is a diagram illustrating the influence of disc concentration in suspension in water according to embodiments of the present disclosure.

FIG. 10 shows the dependency of the disc concentration on $f_c$ and $\delta_{max}$. Different diluted suspensions from 20 to 120×10⁶ of discs per ml of water are tested. The relative light variation is highly sensitive to the disc concentration change and varies linearly from 7% to 31%, while the phase shift remains almost constant for the different disc concentrations. The linear dependency of $\delta_{max}$ and a constant $f_c$ suggest that in this range of disc concentration, each disc 113 acts as individual structure with no interaction and no overlapping with its neighbors. This result is supported by the disc suspension high dilution with a volume fraction varying from 7 to 42×10⁻⁶ and an average inter-disc distance varying from 41 to 23 µm. Therefore, experiments with different dilution in this range can be compared.

Figure 11:
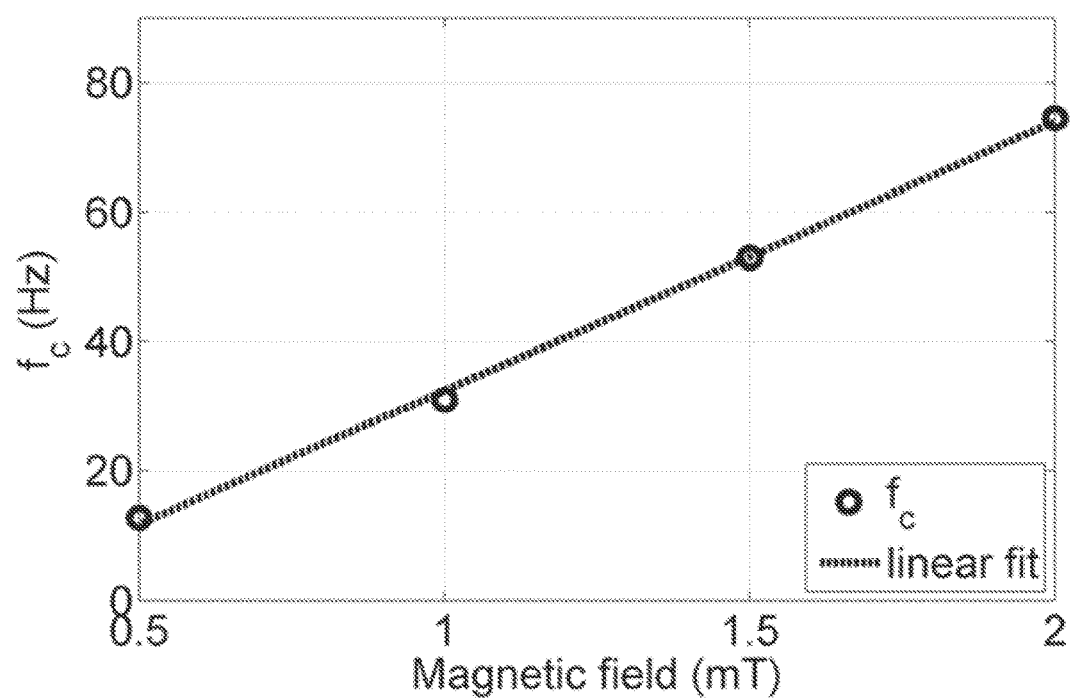
FIG. 11 is a diagram illustrating magnetic field magnitude dependence on characteristic frequency according to embodiments of the present disclosure.

FIG. 11 shows the characteristic frequency evolution by changing the magnetic field magnitude over a range from 0.5 to 2 mT. That data indicates that $f_c$ follows a linear dependence with the field magnitude, at least over the range tested. Indeed, a higher B-field increases the magnetic torque, which shifts the equilibrium rotation rate at a higher frequency. It is noted that in this manner, the characteristic frequency $f_c$ can be tuned by changing the applied B-field, in order to maximize the measurement sensitivity for a given sample.

Figure 12:
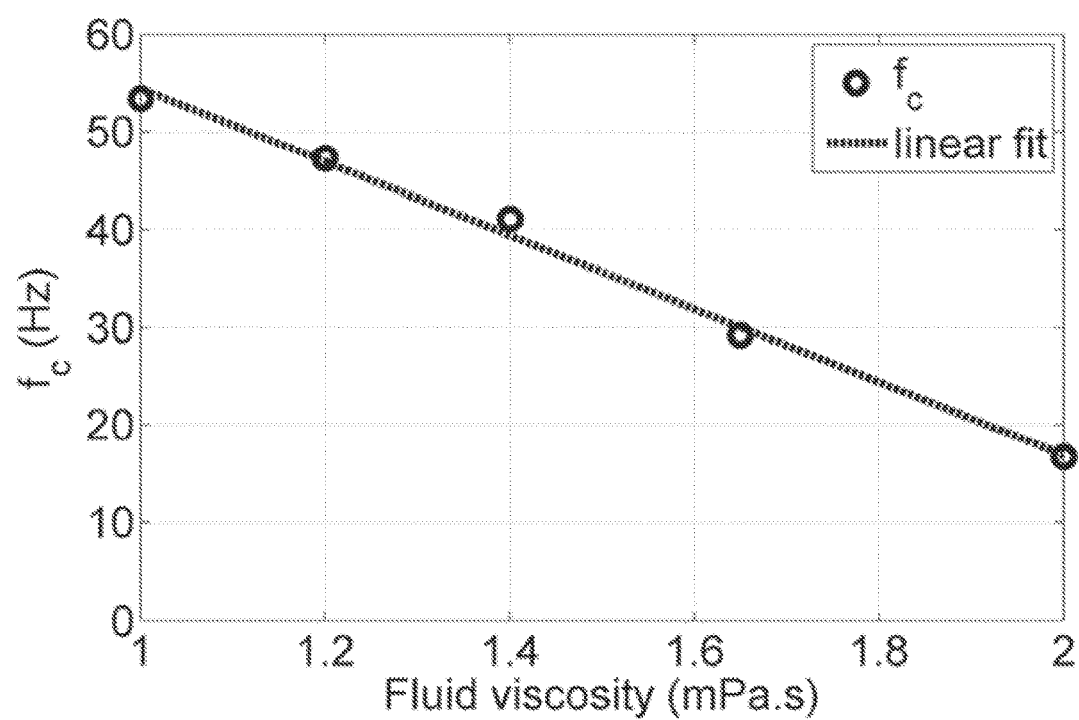
FIG. 12 is a diagram illustrating the dependence of characteristic frequency with fluid viscosity according to embodiments of the present disclosure.

FIG. 12 shows the effect of the fluid viscosity on $f_c$. Different volumes of glycerol are mixed with water (0%-20%) to increase the suspension viscosity from 1 to 2 mPa-s. The characteristic frequency varies linearly from 54 Hz in water to 17 Hz in the more viscous 20% glycerol suspension. Indeed, a larger viscosity increases the hydrodynamic torque, which slows down the rotation of the discs 113.

In accordance with the present disclosure, embodiments of optical interrogation methodology are presented for studying the rotational dynamics of suspended magnetic discs 113 in response to a constant-magnitude rotating magnetic field. Compared to ac susceptometry, such an approach allows for fast and low-cost characterization of fluids 103 with small sample volumes. An exemplary embodiment enables measurement of the phase shift $\phi$ as a function of the frequency and magnitude of the magnetic field. It is noted that the phase shift measurement is independent of experimental variables such as the disc concentration in solution and uncontrolled variations in intensity. Experimental investigation shows a high sensitivity of this method to a fluid viscosity change. Moreover, the main influential parameters of the disc dynamics are introduced by a basic model.

Figure 13:
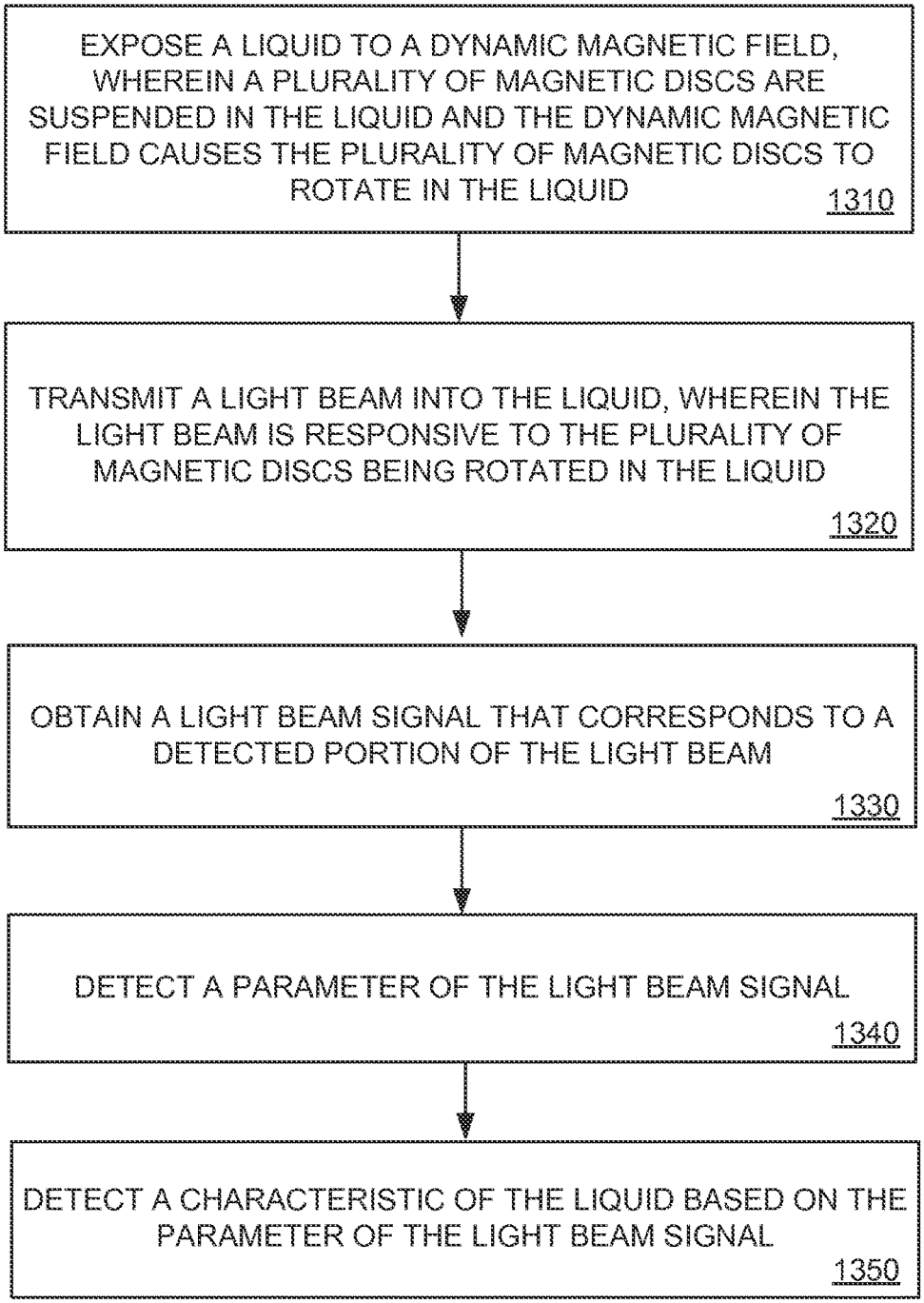
FIGS. 13-14 are flowchart diagrams illustrating exemplary methods according to embodiments of the present disclosure.

Referring now to FIG. 13, an exemplary method in accordance with embodiments of the present disclosure is depicted. As such, a liquid is exposed (1310) to a dynamic magnetic field, wherein a plurality of magnetic discs 113 are suspended in the liquid 103 and the dynamic magnetic field causes the plurality of magnetic discs 113 to rotate in the liquid 103. Next, a light beam 116 is transmitted (1320) into the liquid 103, wherein the light beam 116 is responsive to the plurality of magnetic discs 113 being rotated in the liquid 103. Using at least one computing device, a light beam signal is obtained (1330) that corresponds to a detected portion of the light beam 116. Further, a parameter of the light beam signal is detected (1340), and a characteristic of the liquid 103 is detected (1350) based on the parameter of the light beam signal.

Figure 14:
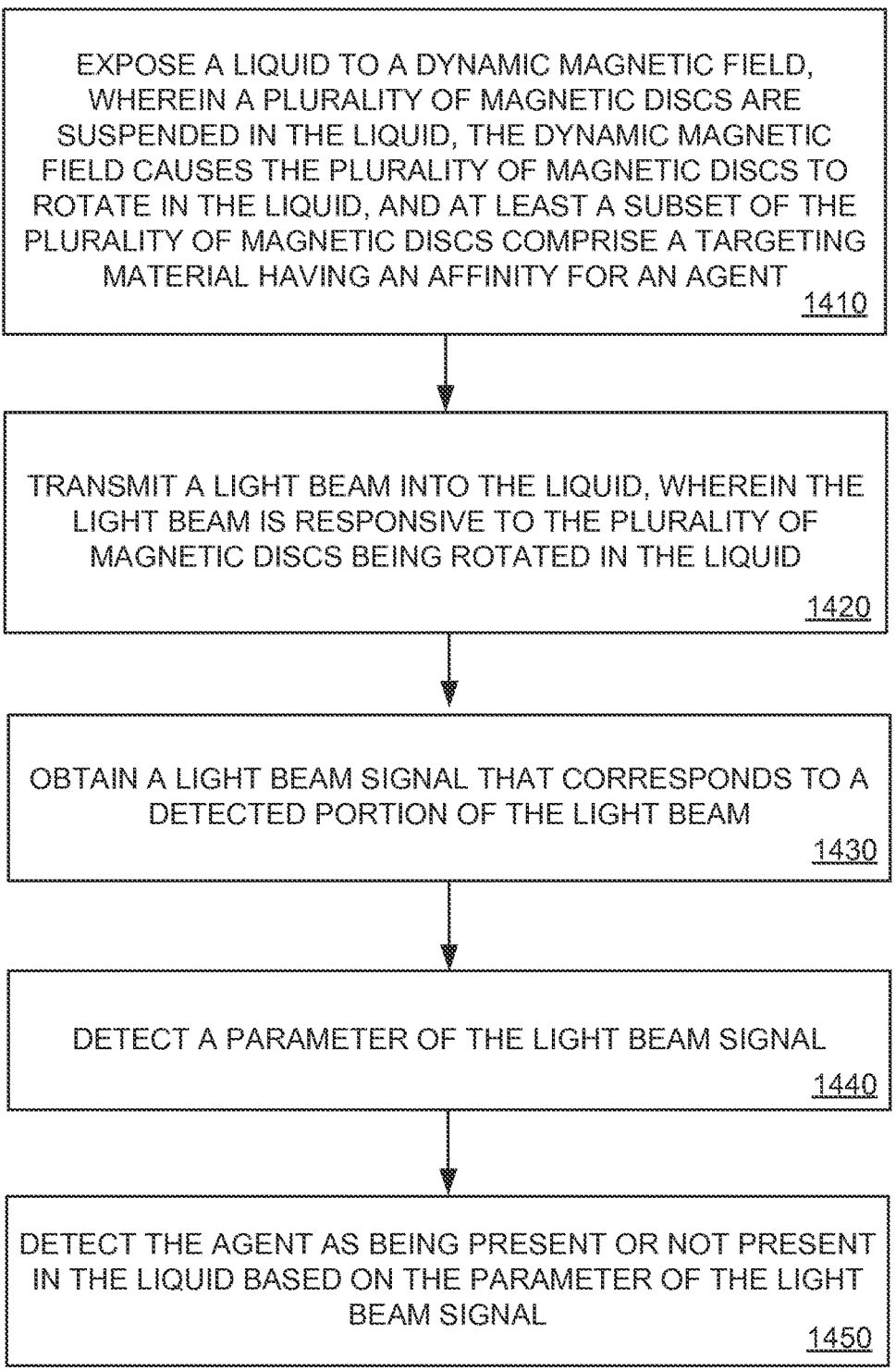

With reference to FIG. 14, shown is a flowchart of an additional exemplary method in according to embodiments of the present disclosure. The method begins with exposing (1410) a liquid 103 to a dynamic magnetic field, wherein a plurality of magnetic discs 113 are suspended in the liquid 103, the dynamic magnetic field causes the plurality of magnetic discs 113 to rotate in the liquid 103, and at least a subset of the plurality of magnetic discs 113 comprise a targeting material having an affinity for an agent. Next, a light beam 116 is transmitted (1420) into the liquid 103, wherein the light beam 116 is responsive to the plurality of magnetic discs 113 being rotated in the liquid 103. Using at least one computing device, a light beam signal is obtained (1430) that corresponds to a detected portion of the light beam 116. Further, a parameter of the light beam 116 is detected (1440), and the agent is detected (1450) as being present or not present in the liquid 103 based on the parameter of the light beam signal.

It is noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'."

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It is emphasized that the above-described embodiments of the present disclosure are merely possible examples of implementations set forth for a clear understanding of the principles of the disclosure. Many variations and modifications may be made to the above-described embodiments without departing substantially from the spirit and principles of the disclosure. All such modifications and variations are intended to be included herein within the scope of this disclosure and protected by the following claims.

Therefore, the following is claimed:

1. A system, comprising:
   a magnetic field generator to expose a liquid to a dynamic magnetic field, wherein a plurality of magnetic discs are suspended in the liquid, wherein the dynamic magnetic field causes the plurality of magnetic discs to rotate in the liquid;
   a light source to transmit a light beam into the liquid, wherein the light beam transmitted into the liquid is responsive to the plurality of magnetic discs being rotated in the liquid;
   a light sensor to generate a light beam signal based on a detected portion of the light beam from the liquid; and
   at least one computing device to:
      detect at least one parameter of the light beam signal, wherein the at least one parameter comprises a phase difference between the dynamic magnetic field and the light beam signal; and
      detect a characteristic of the liquid based on the at least one parameter of the light beam signal.

2. The system of claim 1, wherein the detected portion of the light beam is reflected by the plurality of magnetic discs in the liquid.

3. The system of claim 1, wherein the detected portion of the light beam is transmitted through the liquid.

4. The system of claim 1, wherein the characteristic comprises a viscosity.

5. The system of claim 1, wherein the characteristic comprises a presence of an agent.

6. The system of claim 1, wherein at least a subset of the plurality of magnetic discs comprise a targeting material having an affinity for an agent.

7. The system of claim 1, wherein the dynamic magnetic field is a rotating magnetic field having a substantially constant magnitude.

8. The system of claim 1, wherein the dynamic magnetic field is a rotating magnetic field, wherein a magnitude of the dynamic magnetic field is adjusted while a frequency of the dynamic magnetic field is substantially constant.

9. The system of claim 1, wherein the dynamic magnetic field is a rotating magnetic field, wherein a frequency of the dynamic magnetic field is adjusted while a magnitude of the dynamic magnetic field is substantially constant.

10. The system of claim 1, wherein the at least one parameter further comprises a change in amplitude of an intensity of the light beam signal.

11. The system of claim 1, wherein at least one of the magnetic discs has a diameter of about 1 micrometer.

12. The system of claim 1, wherein at least one of the magnetic discs has a thickness of about 50 nanometers.

13. The system of claim 1, wherein the magnetic field generator comprises a plurality of coils.

14. The system of claim 13, wherein the plurality of coils forms at least one of a Helmholtz coil pair, a solenoid, or any combination thereof.

15. The system of claim 1, wherein the magnetic field generator comprises a plurality of Helmholtz coil pairs.

16. The system of claim 1, wherein the magnetic field generator comprises at least one permanent magnet.

17. The system of claim 1, wherein the plurality of magnetic discs comprises a uniform magnetic material.

18. The system of claim 1, wherein the plurality of magnetic discs have an aspect ratio (diameter/thickness) of at least 10.

19. A method for detecting a characteristic of a liquid, comprising:
   exposing the liquid to a dynamic magnetic field, wherein a plurality of magnetic discs are suspended in the liquid, wherein the dynamic magnetic field causes the plurality of magnetic discs to rotate in the liquid;
   transmitting a light beam into the liquid, wherein the light beam transmitted into the liquid is responsive to the plurality of magnetic discs being rotated in the liquid;
   obtaining, using at least one computing device, a light beam signal that corresponds to a detected portion of the light beam;
   detecting, using the at least one computing device, at least one parameter of the light beam signal, wherein the at least one parameter comprises a phase difference between the dynamic magnetic field and the light beam signal; and detecting, using the at least one computing device, the characteristic of the liquid based on the at least one parameter of the light beam signal.

20. The method of claim 19, wherein the characteristic comprises a viscosity.

21. The method of claim 19, wherein the characteristic comprises a presence of an agent.

22. The method of claim 19, wherein the at least one parameter further comprises a change in amplitude of an intensity of the light beam signal.

23. The method of claim 19, wherein the dynamic magnetic field rotates relative to a container for the liquid.

24. The method of claim 19, further comprising adjusting a frequency of the dynamic magnetic field over a frequency range; and
wherein determining the at least one parameter comprises recording the light beam signal as the frequency of the dynamic field is adjusted.

25. The method of claim 24, wherein a magnitude of the dynamic magnetic field is substantially constant as the frequency is adjusted over the frequency range.

26. The method of claim 19, further comprising adjusting a magnitude of the dynamic magnetic field over a magnitude range while a frequency of the dynamic magnetic field is substantially constant; and
wherein determining the at least one parameter comprises recording the light beam signal as the magnitude of the dynamic magnetic field is adjusted.

27. The method of claim 19, wherein at least one of the magnetic discs has a diameter of about 0.1 micrometers to about 5 micrometers.

28. The method of claim 19, wherein at least one of the magnetic discs has a thickness of about 10 nanometers to about 500 nanometers.

29. The method of claim 19, wherein the magnetic discs include a targeting material having an affinity of an agent.

30. The method of claim 29, wherein the agent comprises at least one of a cell, a tissue, a protein, DNA, RNA, an antibody, an antigen, a predefined compound, or any combination thereof.

31. The method of claim 19, wherein the plurality of magnetic discs comprises a uniform magnetic material.

32. The method of claim 19, wherein the plurality of magnetic discs have a respective diameter within 0.1 micrometer to 5 micrometers, and a respective thickness within 10 nanometers to 500 nanometers.

33. A method for detecting a presence of an agent in a liquid, comprising:
exposing the liquid to a dynamic magnetic field, wherein a plurality of magnetic discs are suspended in the liquid, wherein the dynamic magnetic field causes the plurality of magnetic discs to rotate in the liquid, wherein at least a subset of the plurality of magnetic discs comprise a targeting material having an affinity for the agent;
transmitting a light beam into the liquid, wherein the light beam transmitted into the liquid is responsive to the plurality of magnetic discs being rotated in the liquid;
obtaining, using at least one computing device, a light beam signal that corresponds to a detected portion of the light beam;
detecting, using the at least one computing device, at least one parameter of the light beam signal, wherein the at least one parameter comprises a phase difference between the dynamic magnetic field and the light beam signal; and
detecting, using the at least one computing device, whether the agent is present in the liquid based on the at least one parameter of the light beam signal.

34. The method of claim 33, wherein the agent comprises at least one of a cell, a tissue, a protein, DNA, RNA, an antibody, an antigen, a predefined compound, or any combination thereof.

* * * * *